United States Patent
Vendrell Vila

(10) Patent No.: US 11,801,170 B2
(45) Date of Patent: Oct. 31, 2023

(54) TAMPON APPLICATOR

(71) Applicant: Ramon Vendrell Vila, Balsareny (ES)

(72) Inventor: Ramon Vendrell Vila, Balsareny (ES)

(*) Notice: Subject to any disclaimer, the term of this patent is extended or adjusted under 35 U.S.C. 154(b) by 404 days.

(21) Appl. No.: 17/261,520

(22) PCT Filed: Jul. 16, 2019

(86) PCT No.: PCT/ES2019/070495
§ 371 (c)(1),
(2) Date: Jan. 19, 2021

(87) PCT Pub. No.: WO2020/021137
PCT Pub. Date: Jan. 30, 2020

(65) Prior Publication Data
US 2021/0251816 A1    Aug. 19, 2021

(30) Foreign Application Priority Data
Jul. 24, 2018   (ES) .............................. ES201800443U

(51) Int. Cl.
*A61F 13/26*   (2006.01)
(52) U.S. Cl.
CPC .......... *A61F 13/263* (2013.01); *A61F 13/266* (2013.01)
(58) Field of Classification Search
CPC ...... A61F 13/263; A61F 13/266; A61F 13/26; A61F 13/20; A61F 13/202; A61F 13/55175
See application file for complete search history.

(56) References Cited

U.S. PATENT DOCUMENTS

| | | |
|---|---|---|
| D717,950 S | 11/2014 | Agrawal |
| D719,653 S | 12/2014 | Agrawal |
| 2004/0236265 A1 | 11/2004 | Lamb |
| 2017/0020744 A1* | 1/2017 | Agrawal ............. A61F 13/2097 |

FOREIGN PATENT DOCUMENTS

| | | |
|---|---|---|
| CN | 102655832 A | 9/2012 |
| CN | 107106354 A | 8/2017 |
| WO | 9948453 A1 | 9/1999 |

OTHER PUBLICATIONS

International Search Report dated Dec. 20, 2019 in corresponding application No. PCT/ES2019/070495; 5 pages.
Office Action in corresponding Chinese Patent Application No. 201980048940.9 dated Jan. 28, 2023, 16 pages.

* cited by examiner

*Primary Examiner* — Susan S Su
(74) *Attorney, Agent, or Firm* — Maier & Maier, PLLC

(57) ABSTRACT

A tampon applicator, including: a vaginal insertion tube intended to house the tampon to be used, and a plunger which is mounted coaxially in one end of the tube and which is used to push and release the tampon through a second end of the tube. According to tan embodiment, the applicator can be re-used and the insertion tube includes a side window through which a tampon can be inserted into the tube, before each use of the applicator by the user.

2 Claims, 2 Drawing Sheets

TAMPON APPLICATOR

FIELD

This invention is applicable in the feminine intimate hygiene sector, specifically tampon applicators and refers to a tampon applicator, which comprises a vaginal insertion tube intended to house a tampon to be used, and a plunger which is coaxially mounted in a first end of said tube and which is used to push and release the tampon through a second end of said vaginal insertion tube.

This tampon applicator has technical characteristics aimed at allowing the tampon applicator to be re-used and that the user uses the same applicator to apply the tampons as needed.

BACKGROUND

Currently, tampon applicators used to insert a tampon into the vaginal cavity and prevent the escape of menstrual fluids or of any other type, are widely known.

These applicators comprise a vaginal insertion tube that contains the corresponding tampon and a plunger which is coaxially mounted in a first end of said tube and that is used to push and release the tampon through a second end of the tube during its application.

The tampon applicators currently marketed and known to date include the corresponding tampon in each applicator so that once the tampon is applied, the applicator, generally made of plastic material, is discarded and disposed of generally in an uncontrolled way, which generates environmental problems, especially for fish and for certain animals such as turtles, which ingest them with the consequent risks to their health, including their lives.

The disposal of an applicator per each used tampon represents a large volume of waste.

Therefore, the technical problem that arises is the development of a tampon applicator that allows to satisfactorily solve the problems set out above.

SUMMARY

The tampon applicator object of this invention, being of the above-mentioned type and described in the preamble of the claim 1, has constructive features aimed at allowing the applicator to be re-used, making it unnecessary to dispose of an applicator for each used tampon.

This tampon applicator comprises a vaginal insertion tube designed to contain a tampon to be used, and a plunger which is coaxially mounted in a first end of said tube and is used to push and release the tampon through a second end of the tube.

According to the invention, the tampon applicator of the invention can be re-used and, for this, the insertion tube comprises a side window suitable for introducing a tampon into the tube, prior to each use of the applicator by the user.

This side window allows the user to insert a tampon into the insertion tube prior to its use and to repeat this operation with the same applicator each time a tampon is used.

In this way, the same applicator can be re-used by inserting a new tampon through the side window into the vaginal insertion tube and avoiding the disposal of the applicator each time a tampon is used.

According to the invention, this tampon applicator comprises a protective case suitable for housing the applicator in an inoperative or transport position, in which said applicator does not contain any tampon and the plunger is housed in the vaginal insertion tube, the applicator assembly occupying minimal space.

This protective case allows the applicator to be stored after use, keeping it in adequate hygienic conditions for later use in the event that it has been cleaned after being used or to prevent the applicator from staining objects in the event that it could not have been cleaned immediately after application.

To facilitate cleaning and re-use of the applicator in suitable hygienic conditions, it has been foreseen that both the protective case and the tampon applicator are made of plastic or other hypoallergenic materials and that they can be easily washed or cleaned.

BRIEF DESCRIPTION OF THE DRAWINGS

To complement the description that is being made and in order to facilitate the understanding of the characteristics of the invention, the present specification is accompanied by a set of drawings in which, by way of illustration and not limitation, the following has been represented.

DETAILED DESCRIPTION OF THE EMBODIMENTS

Figure 1:
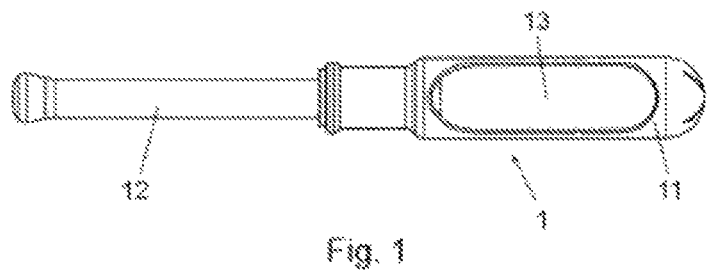
FIG. 1 shows an elevation view of an embodiment of the tampon applicator, according to the invention, with the plunger moved towards the outside of the insertion tube.
Figure 2:
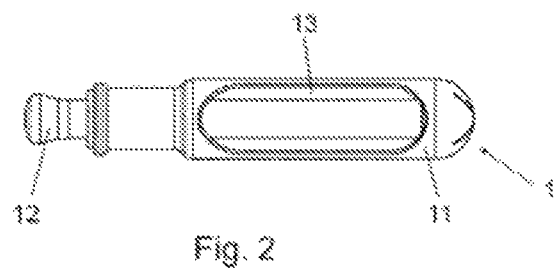
FIG. 2 shows an elevation view of the applicator of the previous figure in an inoperative or transport position.

As can be seen in FIGS. 1 and 2, this tampon applicator, referenced as a whole as (1), comprises a vaginal insertion tube (11) and a plunger (12) mounted in a first end of said tube, with the possibility of axial displacement between the two positions represented in FIGS. 1 and 2.

Figure 3:
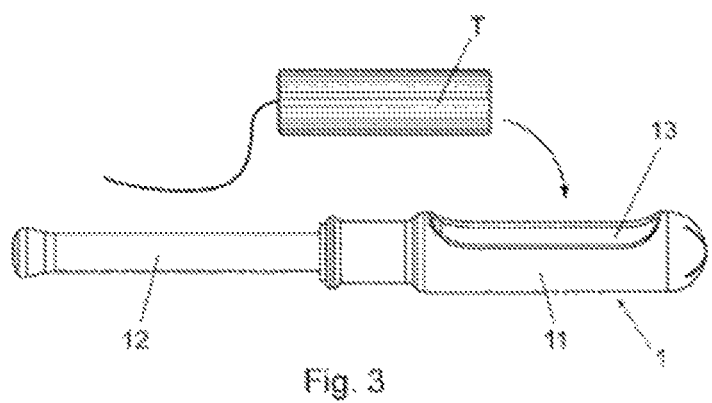
FIG. 3 shows a view of the tampon applicator of the invention during the insertion of a tampon, through the side window of the insertion tube.
Figure 4:
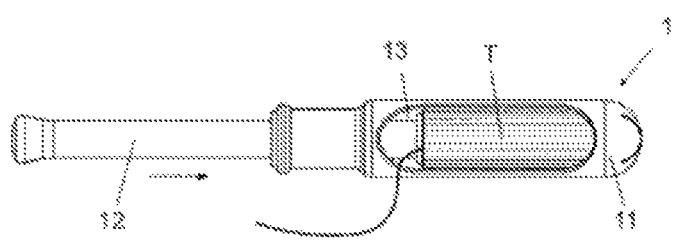
FIG. 4 shows a view of the tampon applicator of the invention during the insertion of a tampon with the tampon housed in the applicator tube ready for use.

This tampon applicator is reusable and, for this effect, the insertion tube (11) comprises a side window (13) suitable for the insertion of a tampon into the tube (11) prior to its use, as shown in FIGS. 3 and 4.

Once a tampon (T) has been inserted into the tube (11), this applicator is used in a conventional way, moving the plunger towards the inside of the tube to push the tampon and release it through the opposite end of the tube (11).

Later, when the user needs to apply a new tampon, it is enough to move the plunger (12) to the initial position, represented in FIG. 1, to leave the side window (13) free and allow the insertion of the new tampon to be used into the tube (11).

Figure 5:
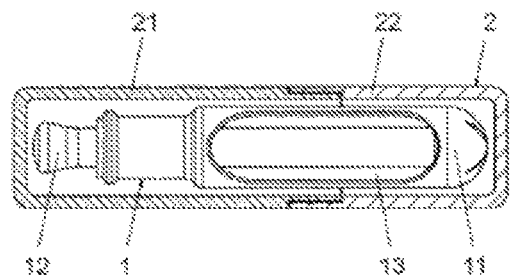
FIG. 5 shows an elevation view of the tampon applicator, in the same inoperative or transport position of FIG. 2, housed in a protective case that has been sectioned along a longitudinal plane.

As shown in FIG. 5, this tampon applicator has a protective case (2) suitable for housing the applicator (1) in the inoperative or transport position, also represented in FIG. 2.

In this position, the applicator occupies a minimum space, which allows the protective case to have dimensions and even a structure and shape similar to a lipstick, allowing it to be transported discreetly.

In the embodiment shown in FIG. 5, the protective case comprises a body (21) and a cover (22) coupled to each other in an axial direction, although said protective case (2) could have any other shape since this does not affect the essence of the invention.

Finally, it should be mentioned that both the applicator (1) and the case (2) are made of a waterproof material, for example, plastic material or another material that can be easily cleaned without deteriorating to guarantee adequate hygienic conditions.

Once the nature of the invention has been sufficiently described, as well as a preferred embodiment, it is stated for the appropriate purposes that the materials, shape, size and arrangement of the elements described may be modified, as long as this does not imply an alteration of the essential features of the invention claimed below.

The invention claimed is:

1. A tampon applicator, comprising:
a vaginal insertion tube configured to contain a tampon to be used, and
a plunger coaxially mounted in a first end of said tube and is used to push and release the tampon through an opening at a second end of the tube;
wherein said applicator is reusable and the insertion tube comprises a side window spaced from both the first end and the second end of the tube, the side window being configured for the insertion of a tampon into the tube while the plunger remains mounted in the first end of the tube, prior to each use of the applicator by the user.

2. The tampon applicator according to claim 1, further comprising a protective case for housing the applicator in an inoperative or transport position, in which the applicator does not contain any tampon and the plunger is housed in the vaginal insertion tube.

\* \* \* \* \*